United States Patent [19]

Gilbard et al.

[11] Patent Number: 4,745,100

[45] Date of Patent: May 17, 1988

[54] STIMULATION OF TEAR SECRETION

[75] Inventors: Jeffrey P. Gilbard, Boston; Darlene A. Dartt, Newton, both of Mass.

[73] Assignee: Eye Research Institute of Retina Foundation, Boston, Mass.

[21] Appl. No.: 830,996

[22] Filed: Feb. 19, 1986

Related U.S. Application Data

[63] Continuation-in-part of Ser. No. 733,967, May 14, 1985, abandoned.

[51] Int. Cl.$^4$ .................. A61K 37/24; A61K 37/28; G02C 7/04
[52] U.S. Cl. .................. 514/12; 514/912; 514/915; 530/308; 424/110
[58] Field of Search .................. 530/308; 514/12, 912, 514/915; 424/110

[56] References Cited

PUBLICATIONS

Gilbard and Dartt, Changes in Rabbit Lacrimal Gland Fluid Osmolarity with Flow Rate. Invest. Ophthalmoh. Vis. Sci., (1982), 23:804–806.

Mauduit et al., Protein Secretion Induced by Isoproterenol or Pentoxifylline in Lacrimal Gland: $Ca^{2+}$ Effects. Am. J. Physiol., (1984), 246:C37–C44.

Stolze and Sommer, Effect of Different Scretagogues in Rabbit Lacrimal Gland Protein Secretion, in *The Preoccular Tear Film in Health, Disease and Contact Lens Wear*, (F. J. Holly, ed.), Dry Eye Institute, Inc., Lubbock, TX, (1986), pp. 409–416.

Dartt et al., Lacrimal Gland Electrolyte and Water Secretion in the Rabbit: Localization and Role of $(Na^+ + K^+)$ Activated ATPase. J. Physiol., (1981), 321:559–569.

Dartt, Cellular Control of Protein Electrolyte, and Water Secretion by the Lacrimal Gland. In *The Preoccular Tear Film in Health, Disease and Contact Lens Wear*. (F. J. Holly, ed.) Dry Eye Institute, Inc., Lubbock, TX, (1986), pp. 358–370.

Friedman et al., B–Adrenergic Receptor Stimulated Peroxide Secretion from Rat Lacrimal Gland, Biochim. Biophys. Acta (1981), 675:40–45.

*Primary Examiner*—J. R. Brown
*Assistant Examiner*—Jacqueline M. Stone
*Attorney, Agent, or Firm*—Lahive & Cockfield

[57] ABSTRACT

A method and preparation for the stimulation of tear secretion. The method involves topically applying to the ocular surface gastrointestinal hormones and/or biologically active peptides and their precursors, derivatives, and fragments which activate vasoactive intestinal peptide receptors of lacrimal gland tissue. The preparation contains a peptide of hormone that activates the vasoactive intestinal peptide receptor such as glucagon or vasoactive intestinal peptide, a vehicle and may also contain an ophthalmic preservative.

6 Claims, 6 Drawing Sheets

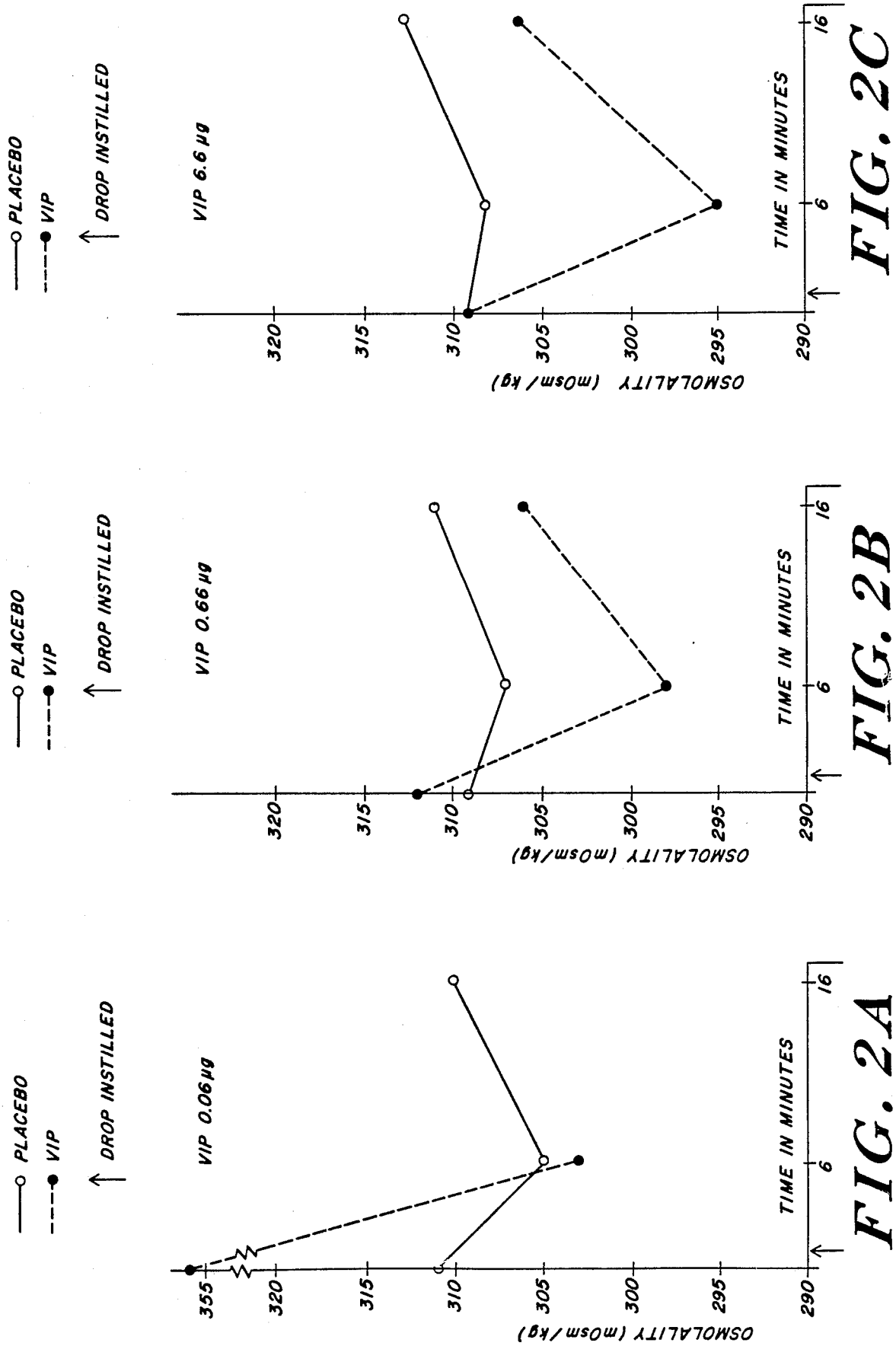

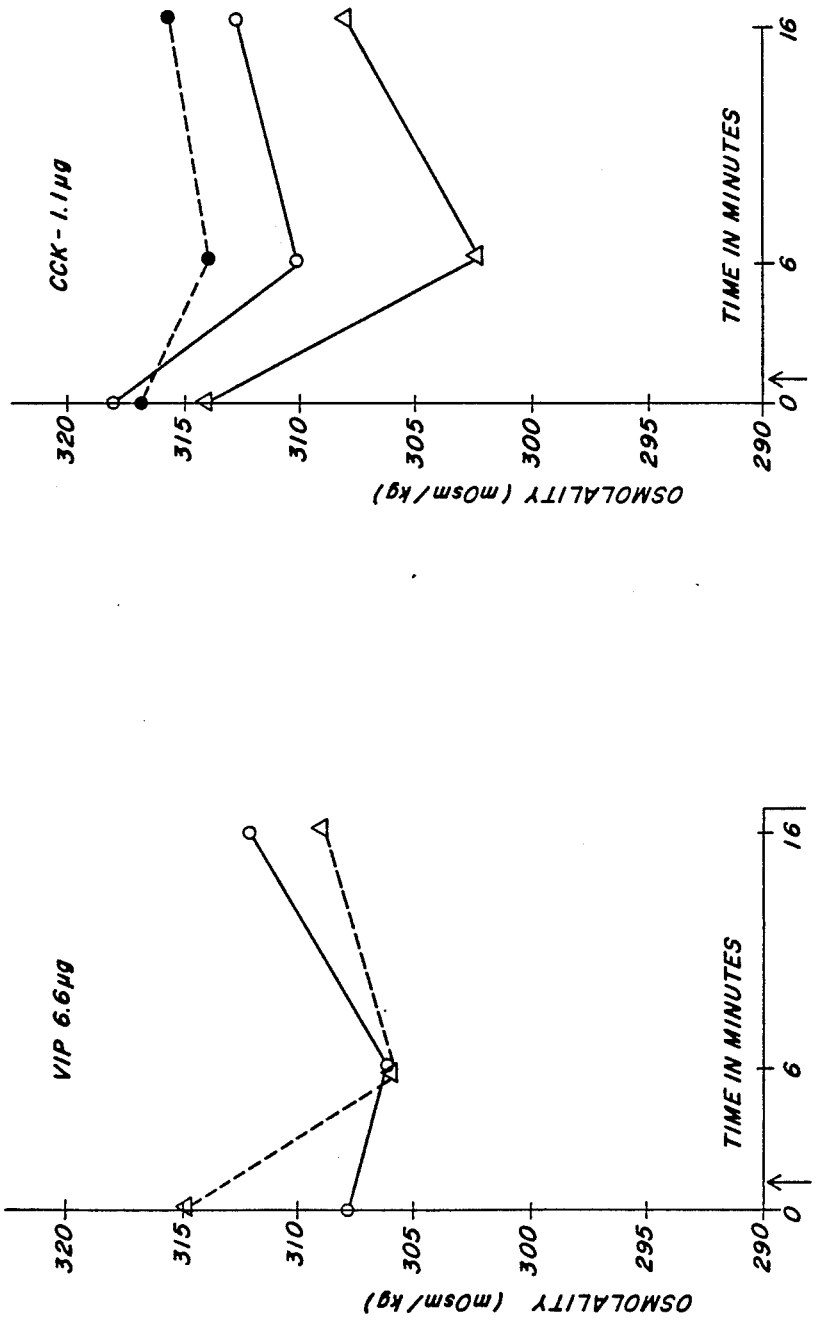

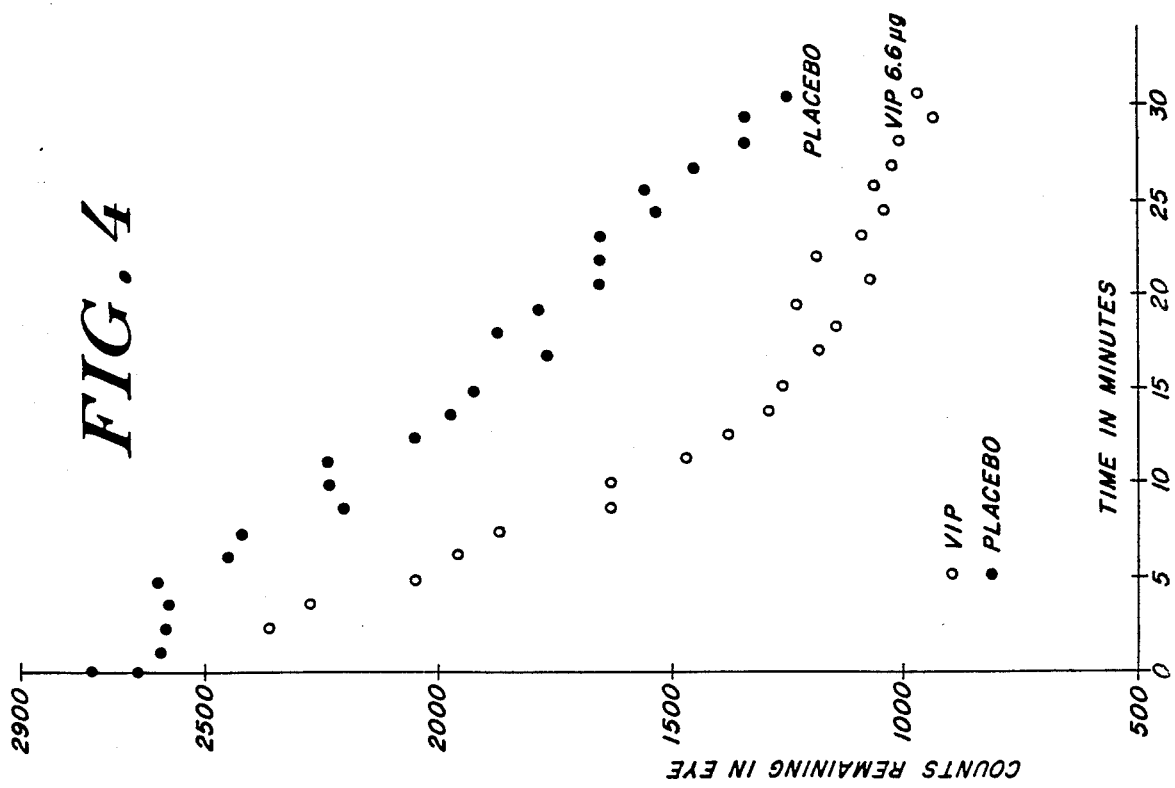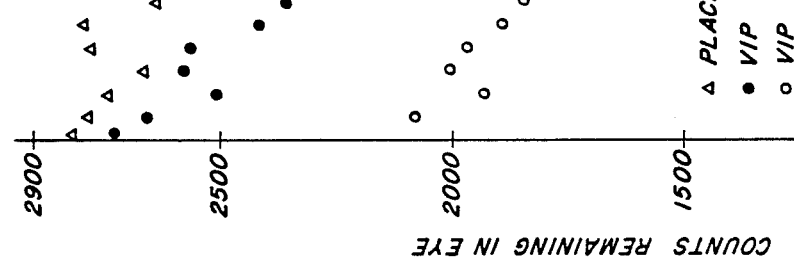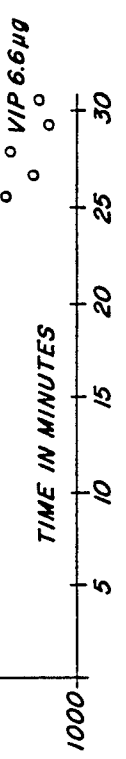

STIMULATION OF TEAR SECRETION

This invention was made with Government support under EY 03373 awarded by the National Eye Institute and is subject to rights of the Government.

BACKGROUND OF THE INVENTION

This application is a continuation-in-part of pending application Ser. No. 733,967, filed May 14, 1985 now abandoned.

This invention relates to a method and preparation for stimulating tear secretion. More particularly, it relates to the stimulation of tear secretion with topically applied gastrointestinal hormones and/or biologically active peptides which activate the vasoactive intestinal peptide (VIP) receptors of lacrimal gland tissue.

There are numerous situations where it is desirable to increase the amount and/or to modify the nature of tear fluid produced by the eye. Illustrative instances include the treatment of a spectrum of dry eye disorders including, but not limited to, keratoconjunctivitis sicca, age-related dry eye, Stevens-Johnson syndrome, ocular cicatricial pemphigoid, blepharitis, neurotrophic ocular surface disease, and corneal exposure. In addition, patients who wear contact lenses may have sub-optimal rates of tear production for optimal contact lens wear. Increased tear production is likely to increase eye comfort and contact lens comfort, and improve contact lens wear. These patients will therefore benefit from agents that increase tear production.

Many different agents have been found to stimulate fluid secretion in the pancreas. Study of the pancreas has defined a spectrum of potential receptors by which agents may be capable of stimulating as well as modifying fluid secretion in other exocrine glands. These receptors have been reviewed by Gardner and Jensen, in the American Journal of Physiology 238:G63-G66, 1980. These receptors in the pancreas, named by any one of several agents that activate them, have been designated (1) Cholinergic (2) Cholecystokinin (CCK) (3) Bombesin (4) Physalaemin (5) Vasoactive Intestinal Peptide (VIP) and (6) Cholera Toxin. It is common to be able to add or delete a portion of the amino-acid chain or even produce small modifications of some of the amino acid sequences and still have hormones or peptides that interact with the same receptor class. Therefore, precursors, derivatives or fragments of these agents may also effectively activate the receptors to stimulate fluid secretion.

In the cat, it is known that VIP is contained in the parenchyma of the lacrimal gland and in the cholinergic sphenopalantine ganglion, but its role, if any, in these locations has been unknown (Johansson and Lundberg, Neuroscience 6:847, 1981; Uddman et al, Invest Opthlamol Vis Sci 19:878, 1980). VIP has also been found in the parenchyma of the rat exorbital lacrimal gland and has been found to stimulate protein secretion in vitro (Dartt et al, Am J Physio 247:G502, 1984). Stolze and Sommer (International Tear Film Symposium, 1984, Lubbock, Tex.) demonstrated that VIP administered intravenously to rabbits can stimulate main (orbital) lacrimal gland secretion.

What is needed are agents which will stimulate tear secretion by topical administration to the ocular surface. A topical mode of administration has several advantages. It eliminates the need for injections in patients with dry eye disorders, thereby decreasing systemic effects, cost of therapy, and the amount of drug needed.

Accordingly, it is an object of this invention to provide a method for stimulating tear secretion by topical administration. It is another object of this invention to provide a method for stimulating lacrimal gland secretion by topically applying compounds to the ocular surface. It is also an object to provide an improved method for the treatment of dry eye disorders. Another object of the present invention is to facilitate the treatment of dry eye disorders without injection. A further object is to provide an improved agent for topical application to improve eye comfort. It is another object of the present invention to provide an improved agent for topical application to enhance contact lens wear and comfort. A further object is to provide a method for increasing the amount of the tear fluid produced by lacrimal gland tissue. Other objects of the invention will in part be obvious and will in part appear hereinafter.

SUMMARY OF THE INVENTION

A method has now been discovered whereby gastrointestinal hormones and biologically active peptides and their precursors, derivatives, and fragments effectively stimulate tear secretion when applied topically to the eye. The method is useful in the treatment of dry eye disorders and facilitates the treatment of dry eye disorders by eliminating the need for injections.

A preparation has also been discovered which when applied topically stimulates lacrimal gland secretion. The preparation contains at least one compound which activates vasoactive intestinal peptide receptors of the lacrimal gland tissue, contains an ophthalmic preservative, and typically contains a physiologically compatible vehicle.

The method involves topical administration to the ocular surface of compounds that activate vasoactive intestinal peptide receptors of lacrimal gland tissue to stimulate tear secretion. These compounds include gastrointestinal hormones and gastrointestinal hormone precursors, derivatives, and fragments, biologically active peptides, and biologically active peptide precursors, derivatives, and fragments. These compounds may be used alone or in combination with one another. Preferred compounds are glucagon, its active precursors, derivatives, fragments, and analogues. Vasoactive intestinal peptide (VIP) may also be used, as can its active precursors, derivatives, analogues and fragments. Other preferred compounds include porcine histidine isoleucine amide-containing peptide (PHI), peptide having an amino terminal histidine and a carboxy terminal methionine amide (PHM-27), secretin, and helodermin and their active precursors, derivatives, and fragments.

Several modes of topical administration may be used in the practice of the invention. For example, the compounds can be administered topically to the eye as a drop, or within ointments, gels, or liposomes. Further, the compounds can be infused into the tear film by means of a pump-catheter system. In other embodiments the compounds are attached to and/or incorporated into contact lenses or contained within or carried by continuous or other selective-release devices including membranes.

The development of agents effective in stimulating lacrimal secretion when applied topically to the eye is unexpected for several reasons. First, the main lacrimal gland is not exposed to the surface of the eye; rather, it lies separated from the ocular surface by a relatively great diffusion distance. The main lacrimal gland is connected to the surface only through a series of microscopic ducts. Therefore, while drugs injected vascularly can reach the main lacrimal gland parenchyma, it is unlikely that topically applied drugs will do so. Second, although there are microscopic nests of accessory lacrimal gland tissue within the conjunctiva, one expects that drugs will not penetrate the luminal tight junctions of the duct and acinar cells to the deep basolateral membranes. It is assumed, based on study of the pancreas, that receptors which initiate secretion are located in the deep basolateral membranes. Third, given that the accessory glands are understood to function somewhat independently from the main lacrimal gland, it is deemed unlikely that drugs that stimulate the main gland would stimulate the accessory glands even if penetration were adequate.

BRIEF DESCRIPTION OF THE DRAWINGS

FIG. 1A is a graph of the osmolality of tear samples, as a function of time, taken from a rabbit eye treated with 10 µl of buffer solution and, subsequently, the same eye treated in accordance with the invention with 10 µl of buffer solution containing $2 \times 10^{-8}$ M VIP.

FIG. 1B is a graph of the osmolality of tear samples, as a function of time, taken from a rabbit eye treated with 10 µl of buffer solution and, subsequently, the same eye treated in accordance with the invention with 10 µl of buffer solution containing $2 \times 10^{-7}$ M VIP.

FIG. 1C is a graph of the osmolality of tear samples, as a function of time, taken from a rabbit eye treated with 10 µl of buffer solution and, subsequently, the same eye treated in accordance with the invention with 10 µl of buffer solution containing $2 \times 10^{-6}$ M VIP.

FIGS. 2A, 2B, and 2C represent results obtained from further practice of the invention with rabbits.

FIG. 2A is a graph of the osmolality of tear samples, as a function of time, taken from a rabbit eye treated with 10 µl of buffer solution and, subsequently, the same eye treated in accordance with the invention with 10 µl of buffer solution containing $2 \times 10^{-8}$ M VIP.

FIG. 2B is a graph of the osmolality of tear samples, as a function of time, taken from a rabbit eye treated with 10 µl of buffer solution and, subsequently, the same eye treated in accordance with the invention with 10 µl of buffer solution containing $2 \times 10^{-7}$ M VIP.

FIG. 2C is a graph of the osmolality of tear samples, as a function of time, taken from a rabbit eye treated with 10 µl of buffer solution and, subsequently, the same eye treated in accordance with the invention with 10 µl of buffer solution containing $2 \times 10^{-6}$ M VIP.

FIGS. 3A and 3B represent results obtained from further practice of the invention with rabbits.

FIG. 3A is a graph of the osmolality of tear samples, as a function of time, taken from a rabbit eye treated with 10 µl of buffer solution and, subsequently, the same eye treated in accordance with the invention with 10 µl of buffer solution containing $2 \times 10^{-6}$ M VIP.

FIG. 3B is a graph of the osmolality of tear samples, as a function of time, taken from a rabbit eye treated with 10 µl of buffer solution, followed by treatment with 10 µl of buffer solution containing $2 \times 10^{-4}$ M CCK, and, subsequently, the same eye treated in accordance with the invention with 10 µl of buffer solution containing $2 \times 10^{-6}$ M VIP.

FIG. 4 is a graph of the radioactivity present in the tear film, as a function of time, after instillation of 10 µl of a radioactive buffer solution, and after instillation of 10 µl of a radioactive buffer solution containing $2 \times 10^{-6}$ M VIP, demonstrating the elimination of tracer substance from the tear film.

FIG. 5 is a graph of radioactivity present in the tear film, as a function of time, after instillation of 10 µl of a radioactive, buffer solution and 10 µl of a radioactive buffer solution containing $2 \times 10^{-6}$ M VIP demonstrating the elimination of tracer substance from the tear film.

FIG. 6A is a graph of the osmolality of tear samples as a function of time taken from a rabbit eye treated with 10 µl of buffer solution and the same eye treated in accordance with the invention with 10 µl of buffer solution containing $2 \times 10^{-6}$ M glucagon.

FIG. 6B is a graph of the osmolality of tear samples, as a function of time, taken from a rabbit eye treated with 10 µl of buffer solution and, subsequently, the same eye treated in accordance with the invention with 10 µl of buffer solution containing $2 \times 10^{-5}$ M glucagon.

FIG. 6C is a graph of the osmolality of tear samples, as a function of time, taken from a rabbit eye treated with 10 µl of buffer solution and, subsequently, the same eye treated in accordance with the invention with 10 µl of buffer solution containing $2 \times 10^{-4}$ M glucagon.

FIG. 7A is a graph of the osmolality of tear samples, as a function of time, taken from a rabbit eye treated with 10 µl of buffer solution and, subsequently, the same eye treated in accordance with the invention with 10 µl of buffer solution containing $2 \times 10^{-7}$ M secretin.

FIG. 7B is a graph of the osmolality of tear samples, as a function of time, taken from a rabbit eye treated with 10 µl of buffer solution and, subsequently, the same eye treated in accordance with the invention with 10 µl of buffer solution containing $2 \times 10^{-6}$ M secretin.

FIG. 7C is a graph of the osmolality of tear samples as a function of time taken from the eye treated with 10 µl of buffer solution and the same eye treated with 10 µl of buffer solution containing $2 \times 10^{-5}$ M secretin.

DESCRIPTION OF THE INVENTION

Figure 1C:
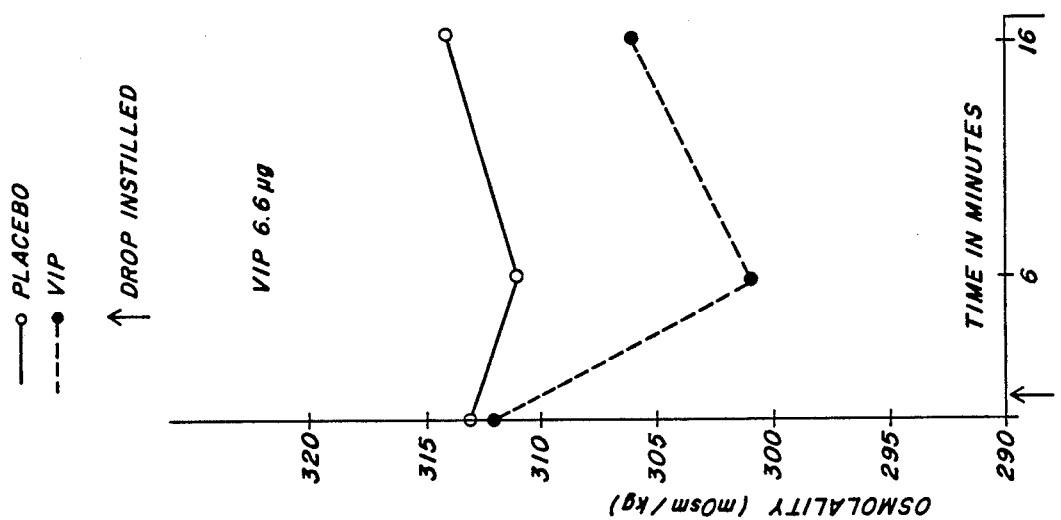
FIGS. 1A, 1B, and 1C represent results obtained from practice of the invention with rabbits.
Figure 1B:
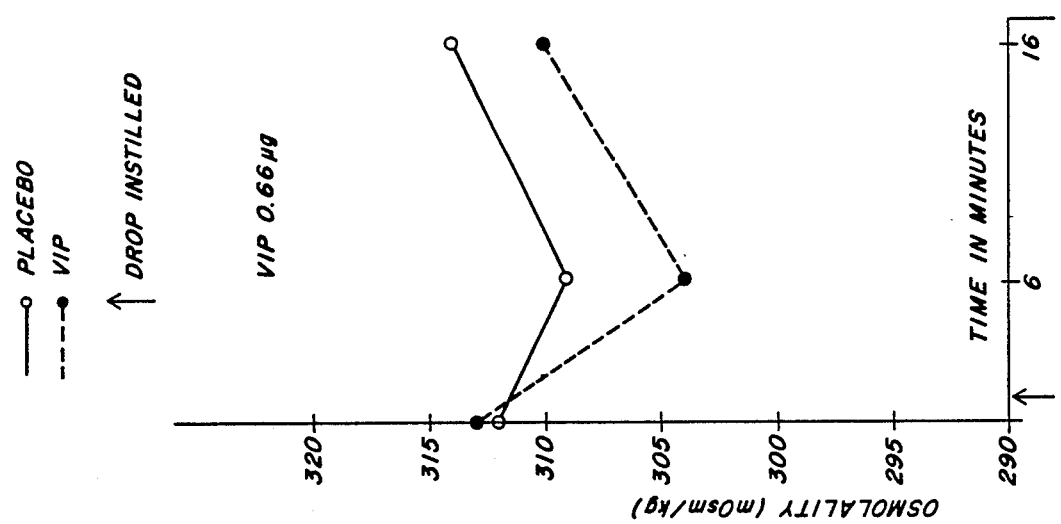
Figure 1A:
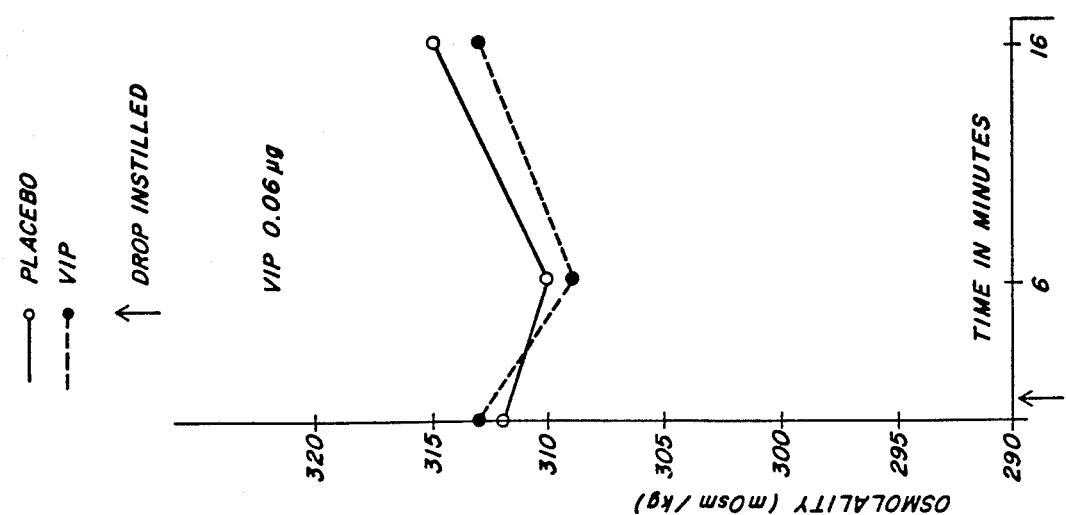

In accordance with the invention, tear secretion is stimulated with topically applied gastrointestinal hormones, biologically active peptides, their precursors, fragments, derivatives, or with combinations of these hormones and peptides, that activate the VIP receptors of lacrimal gland tissue to stimulate tear secretion. With regard to the VIP receptor, these gastrointestinal hormones and biologic peptides can include but are not limited to vasoactive intestinal peptide (VIP), porcine histidine isoleucine amide-containing peptide (PHI), PHM-27, secretin, glucagon, helodermin and their active precursors and active fragments and active derivatives.

A preparation according to the invention can, by way of non-limiting illustration, be applied to the eye in animals and humans as a drop or within ointments, gels, or liposomes. Further, the compounds can be infused into the tear film via a pump-catheter system. In other embodiments, the compounds can be contained within or carried by continuous or other selective-release devices, for example, membranes, such as but not limited to those used in the Ocusert ® system (Alza Corp., Palo Alto, Calif.). They also can be attached to, carried by and/or contained within contact lenses that are placed on the eye. In general, it is desired that the mode of application be such that the compound enters the tear film or otherwise makes contact with the surface of the eye.

In vivo examples of the invention were conducted on rabbits with dry eyes. The dry eye disorder is created by surgically closing the duct that carries fluid from the main lacrimal gland to the tear film and surgically removing the nictitans and harderian glands. This leaves intact only the accessory glands that lie on the ocular surface. These rabbits develop increased tear film osmolality soon after the operation, a finding that is understood to be due to decreased tear production, and that is characteristic of dry eye. It is recognized that results of ophthalmologic tests using rabbits has close correlation with humans, and therefore the results carry over to humans.

The effect of topically applied isotonic buffer solution with and without VIP on tear film osmolality was studied in the dry eye rabbit. All test drops were ten $\mu l$ in volume and were applied in each case six minutes after the instillation of proparacaine, which anesthetizes the surface of the eye and prevents reflex tearing. Tear samples were taken with a micropipette system, in the manner described in the article entitled "Osmolarity of Tear Microvolumes in Keratoconjunctivitis Sicca", by Gilbard et al, Arch Ophthalmol 96:677, 1978. Osmolality was measured by freezing-point depression.

The following protocol was used for each drop tested. Six minutes prior to instillation of the test drop proparacaine was instilled. At zero time a tear sample was taken for measurement of osmolality. At one minute the test drop was instilled. At six and at sixteen minutes, tear samples were taken for osmolality measurements. The procedure for instilling each test drop is that the drop of buffered solution was first instilled in the dry eye and measurements were taken followed by a drop of buffered solution containing VIP. The following test drops were instilled: (1) buffer solution, (2) buffer solution containing $2\times10^{-8}$ M VIP, (3) buffer solution, (4) buffer solution containing $2\times10^{-7}$ M VIP, (5) buffer solution, (6) buffer solution containing $2\times10^{-6}$ M VIP. The results are shown in FIGS. 1A, 1B, and 1C and FIGS. 2A, 2B, and 2C, where FIGS. 1 and 2 each represent the results obtained from the same rabbit.

As shown in FIGS. 1 and 2, buffer solution containing VIP lowers the tear film osmolality more effectively than buffer solution alone. The Figures also indicate that VIP produced a dose-dependent decrease in tear film osmolality, and the decrease was strikingly more pronounced than the effect of buffer alone. This reflects a VIP stimulated dose-dependent increase in tear secretion.

In a similar protocol the effect of topically applied CCK on tear secretion was tested. CCK, like VIP, had been found to stimulate lacrimal gland secretion when administered intra-arterially. CCK did not lower tear osmolality more effectively than a placebo, as shown in FIG. 3B. In the same experiment, VIP decreased tear film osmolality more effectively than a placebo in one of two trials. It accordingly appears, without apparent reason, that CCK, unlike VIP, does not stimulate tear secretion when applied topically to the eye.

In a separate example, dry eye rabbits were studied by examining the rate of elimination of a tracer substance technectium, $Tc^{99m}$, as sodium pertechnetate from the tear film. Essentially equivalent counts of $Tc^{99m}$ were placed in ten microliters of, in some instances, a buffer solution to serve as a control, and in other instances, a buffer solution containing $2\times10^{-6}$ M VIP. Radioactivity present in the tear film was measured over contiguous fifteen second periods for thirty minutes with a gamma camera, and the measurements stored on a computer. The following protocol was used: Rabbits were anesthetized with IM rompun and ketamine. At zero time proparacaine was applied. At five minutes, the radioactive buffer with VIP was instilled in the eye. Radioactivity present in the tear film was then recorded as described. After thirty minutes, proparacaine was again instilled in the eye and the procedure repeated with radioactive buffer alone. As shown in FIG. 4, the slope of the elimination curve for VIP over the first fifteen minutes after drop instillation is markedly steeper than the curve for buffer without VIP (slope for first 15 minutes is $-1.65$ for VIP vs $-0.82$ for placebo). This increased rate of tracer washout is understood to be indicative of increased tear secretion. In a second similar experiment, the effect of VIP was first tested, and then radioactive buffer alone, and then the effect of VIP again. As shown in FIG. 5, the slope of the elimination curves for both VIP tests were substantially steeper than for radioactive buffer alone, confirming again that topically applied VIP stimulates tear secretion.

In separate experiments, the effect of topically applied isotonic buffer solution with or without glucagon or secretin on tear film osmolality was studied in dry eye rabbits. All test drops were ten microliters in volume. Tear osmolality was measured one minute prior to drop instillation and five and fifteen minutes after drop instillation. A drop of buffered solution was first instilled in the dry eye and measurements were taken followed by a drop of buffered solution containing glucagon or secretin, depending on the test.

Figure 6C:
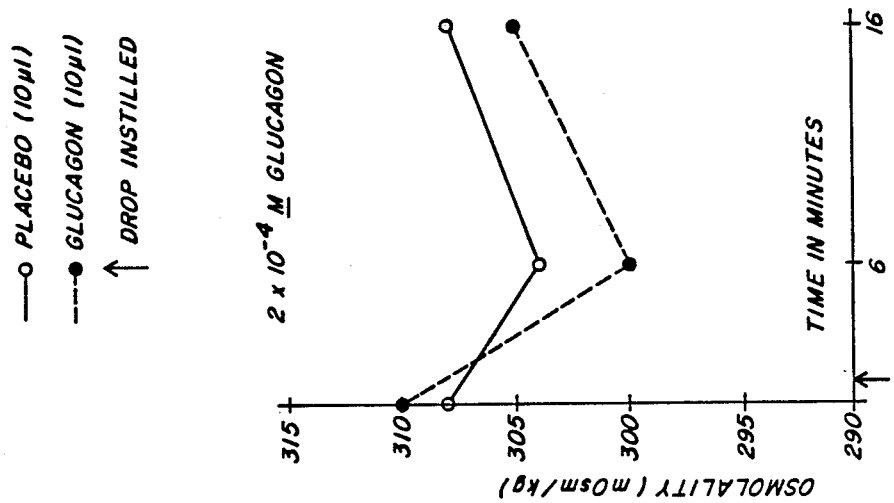
FIGS. 6A, 6B and 6C represent results obtained from further practice of the invention with rabbits.
Figure 6B:
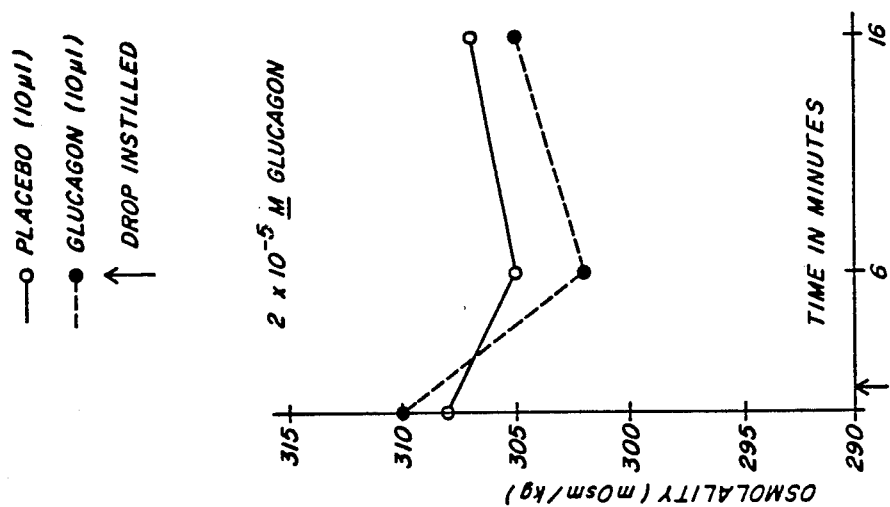
Figure 6A:
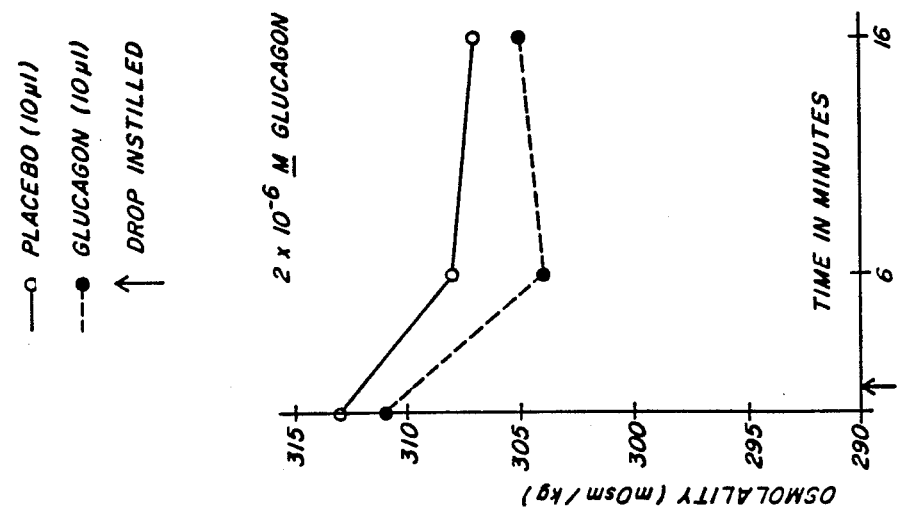

The effect of topically applied glucagon was studied with the instillation of drops in the following order: (1) buffer solution, (2) buffer solution containing $2\times10^{-6}$ M glucagon, (3) buffer solution, (4) buffer solution containing $2\times10^{-5}$ M glucagon, (5) buffer solution, (6) buffer solution containing $2\times10^{-4}$ M glucagon. The results are shown in FIGS. 6A, 6B, and 6C, all of which represent results from the same rabbit. As shown in FIG. 6, buffer solution containing glucagon lowers tear film osmolality more effectively than buffer solution alone. The figure also indicates that glucagon produces a dose-dependent decrease in tear film osmolality and the decrease is more pronounced than the effect of buffer alone. This reflects a glucagon stimulated dose-dependent increase in tear secretion.

Figure 7C:
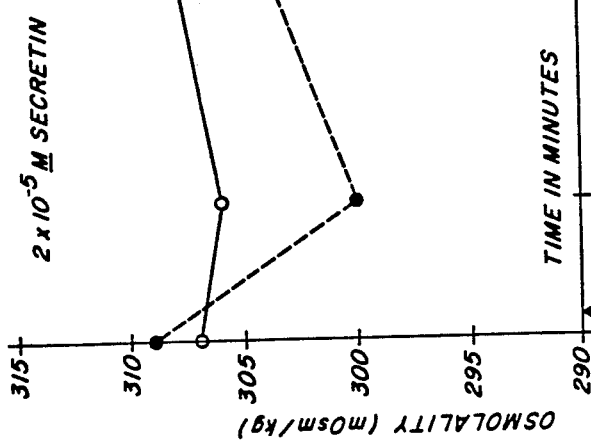
FIGS. 7A, 7B and 7C represents results obtained from further practice of the invention with rabbits.
Figure 7B:
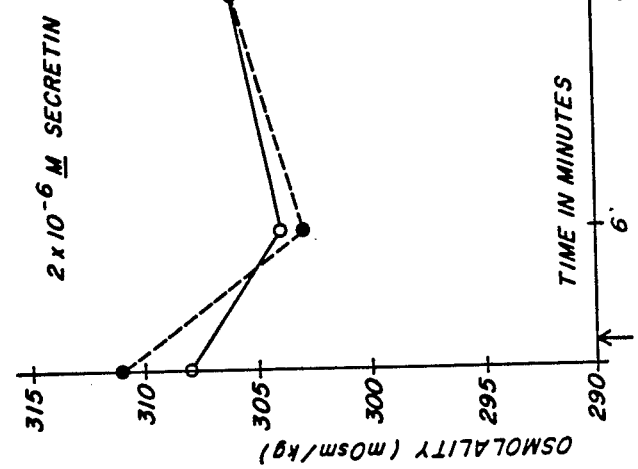
Figure 7A:
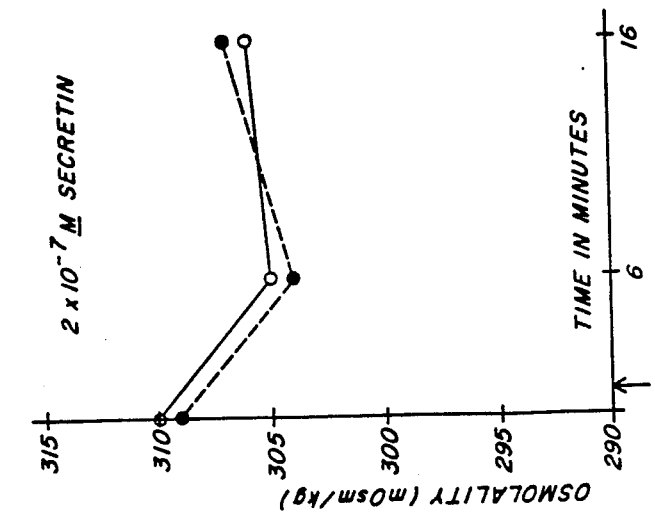

The effect of topically applied secretin was studied with the instillation of drops in the following order: (1) buffer solution (2) buffer solution containing $2\times10^{-7}$ M secretin, (3) buffer solution, (4) buffer solution containing $2\times10^{-6}$ M secretin, (5) buffer solution, (6) buffer solution containing $2\times10^{-5}$ M secretin. The results are shown in FIGS. 7A, 7B, and 7C, all of which represents results from the same rabbit. As shown in FIG. 7, buffer solution containing secretin lowers tear film osmolality more effectively than buffer solution alone. The Figure also indicates that secretin produces a dose-dependent decrease in tear film osmolality and the decrease is more pronounced than the effect of buffer alone. This reflects a secretin stimulated dose-dependent increase in tear secretion.

Further in accordance with the invention, a tear-stimulation preparation is made by combining a gastrointestinal hormone and/or biologically active peptide which activates the VIP receptors of lacrimal gland tissue with an appropriate preservative. The preparation may also contain a physiologically compatible ophthalmic vehicle as those skilled in the art can select using conventional criteria. The vehicles may be selected from the known ophthalmic vehicles which include but are not limited to water, polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, vegetable fats such as peanut oil, polymers of acrylic acid such as carboxypolymethylene gel, polysaccharides such as dextrans, and glycosaminoglyçans such as sodium hyaluronate and salts such as sodium chloride and potassium chloride. One preferred vehicle is the non-toxic ophthalmic preparation with has the following composition: about 22.0 to 43.0 millimoles of potassium per liter; about 29.0 to 50.0 millimoles of bicarbonate per liter; about 130.0 to 140.0 millimoles of sodium per liter; and about 118.0 to 136.5 millimoles of chloride per liter.

Preferred preservatives are physiologically compatible and do not inactivate the hormone or peptide. Preservatives include but are not limited to alcohols such as chlorobutanol, though other appropriate preservatives known to those skilled in the art may be used. As known, glucagan requires the additives glycerin and lactose to render it soluble.

It will thus be seen that the objects set forth above, among those made apparent from the preceding description, are efficiently attained. Since certain changes may be made in carrying out the above method, and in formulating the foregoing preparation, without departing from the scope of the invention, it is intended that all matter contained in the above description be interpreted as illustrative and not in a limiting sense.

Accordingly, the invention may be embodied in other specific forms without departing from the scope or spirit thereof.

What is claimed is:

1. A method of stimulating in vivo fluid secretion from human accessory lacrimal glands comprising the step of topical administration to the ocular surface of an effective amount of a preparation which includes a compound that activates the vasoactive intestinal peptide receptors of said accessory lacrimal glands, said compound selected from a group consisting a glucagon, vasoactive intestinal peptide, and their active precursors, derivatives, analogs, and fragments.

2. The method of claim 1 wherein said topical administration comprises infusion of said preparation to said ocular surface from a device selected from a group consisting of a pump-catheter system, a selective release device, and a contact lens.

3. The method of claim 1 wherein said preparation for topical administration further comprises dispersion of said compound in a carrier vehicle selected from a group consisting of drops of liquid, gels, ointments, and liposomes.

4. A method of stimulating in vivo fluid secretion from human accessory lacrimal glands comprising the step of topical administration to the ocular surface of an effective amount of a preparation which includes a compound that activates the vasoactive intestinal peptide receptors of said accessory lacrimal glands, said compound selected from a group consisting of secretin, and its active precursors, derivatives, analogs, and fragments.

5. The method of claim 4 wherein said topical administration comprises infusion of said preparation to said ocular surface from a device selected from a group consisting of a pump-catheter system, a selective release device, and a contact lens.

6. The method of claim 4 wherein said preparation for topical administration further comprises dispersion of said compound in a carrier vehicle selected from a group consisting of drops of liquid, gels, ointments, and liposomes.

* * * * *

UNITED STATES PATENT AND TRADEMARK OFFICE
CERTIFICATE OF CORRECTION

PATENT NO. : 4,745,100
DATED : May 17, 1988
INVENTOR(S) : Gilbard et al.

It is certified that error appears in the above-identified patent and that said Letters Patent is hereby corrected as shown below:

At Column 8, Line 11, delete "a" and insert --of--.(2nd oc.)

At Column 7, Line 24, delete "with" and insert --which--.

Signed and Sealed this

Twenty-first Day of February, 1989

*Attest:*

DONALD J. QUIGG

*Attesting Officer*          *Commissioner of Patents and Trademarks*